(12) United States Patent
Madgavkar et al.

(10) Patent No.: US 9,861,967 B2
(45) Date of Patent: Jan. 9, 2018

(54) DEHYDROAROMATIZATION CATALYST, METHOD OF MAKING AND USE THEREOF

(71) Applicant: SHELL OIL COMPANY, Houston, TX (US)

(72) Inventors: Ajay Madhav Madgavkar, Katy, TX (US); Ann Marie Lauritzen, Houston, TX (US)

(*) Notice: Subject to any disclaimer, the term of this patent is extended or adjusted under 35 U.S.C. 154(b) by 38 days.

(21) Appl. No.: 14/652,460

(22) PCT Filed: Dec. 17, 2013

(86) PCT No.: PCT/US2013/075550
§ 371 (c)(1),
(2) Date: Jun. 16, 2015

(87) PCT Pub. No.: WO2014/099844
PCT Pub. Date: Jun. 26, 2014

(65) Prior Publication Data
US 2015/0321182 A1    Nov. 12, 2015

Related U.S. Application Data

(60) Provisional application No. 61/739,089, filed on Dec. 19, 2012.

(51) Int. Cl.
| | |
|---|---|
| *B01J 29/06* | (2006.01) |
| *B01J 20/18* | (2006.01) |
| *B01J 29/44* | (2006.01) |
| *B01J 20/28* | (2006.01) |
| *B01J 20/30* | (2006.01) |
| *B01J 29/70* | (2006.01) |
| *B01J 29/40* | (2006.01) |
| *B01J 29/65* | (2006.01) |
| *B01J 29/67* | (2006.01) |
| *B01J 29/74* | (2006.01) |
| *C07C 2/76* | (2006.01) |
| *B01J 37/02* | (2006.01) |
| *B01J 37/08* | (2006.01) |
| *B01J 35/10* | (2006.01) |
| *B01J 35/02* | (2006.01) |
| *B01J 37/00* | (2006.01) |

(52) U.S. Cl.
CPC .............. *B01J 29/44* (2013.01); *B01J 20/18* (2013.01); *B01J 20/183* (2013.01); *B01J 20/28004* (2013.01); *B01J 20/28011* (2013.01); *B01J 20/28019* (2013.01); *B01J 20/28071* (2013.01); *B01J 20/3042* (2013.01); *B01J 20/3071* (2013.01); *B01J 29/40* (2013.01); *B01J 29/65* (2013.01); *B01J 29/67* (2013.01); *B01J 29/7003* (2013.01); *B01J 29/7034* (2013.01); *B01J 29/7046* (2013.01); *B01J 29/7469* (2013.01); *B01J 29/7492* (2013.01); *C07C 2/76* (2013.01); *B01J 29/405* (2013.01); *B01J 29/655* (2013.01); *B01J 29/7084* (2013.01); *B01J 29/7096* (2013.01); *B01J 35/023* (2013.01); *B01J 35/1038* (2013.01); *B01J 37/0009* (2013.01); *B01J 37/0207* (2013.01); *B01J 37/0236* (2013.01); *B01J 37/08* (2013.01); *B01J 2229/186* (2013.01); *B01J 2229/20* (2013.01); *B01J 2229/37* (2013.01); *B01J 2229/42* (2013.01); *C07C 2521/04* (2013.01); *C07C 2529/44* (2013.01)

(58) Field of Classification Search
CPC . B01J 29/068; B01J 29/40; B01J 29/44; B01J 29/405; B01J 29/65; B01J 29/655; B01J 29/67; B01J 29/7034; B01J 29/7046; B01J 29/7469; B01J 29/7492; B01J 29/7084; B01J 29/7096; B01J 2229/186; B01J 2229/42; B01J 37/0009; B01J 37/08; B01J 37/0201; B01J 37/024; C07C 2521/04; C07C 2529/44; C07C 2529/068; C07C 2529/40; C07C 2529/70; C07C 2529/74
USPC .......................... 502/64, 66, 71, 73, 74, 77
See application file for complete search history.

(56) References Cited

U.S. PATENT DOCUMENTS

| | | | | |
|---|---|---|---|---|
| 3,525,699 | A * | 8/1970 | Koppel | B01J 21/02 208/112 |
| 4,029,716 | A * | 6/1977 | Kaeding | C07C 6/123 585/407 |
| 4,350,835 | A * | 9/1982 | Chester | B01J 29/40 502/61 |
| 4,855,522 | A | 8/1989 | Diaz | |
| 4,950,828 | A | 8/1990 | Shum | |
| 5,026,937 | A | 6/1991 | Bricker | |
| 5,053,570 | A | 10/1991 | Soto et al. | |
| 6,107,534 | A | 8/2000 | Drake et al. | |
| 6,156,689 | A * | 12/2000 | Kimble | B01J 29/40 502/202 |
| 7,462,338 | B2 * | 12/2008 | Southward | B01D 53/944 423/213.5 |
| 2005/0036295 | A1 | 2/2005 | Beeckman et al. | |
| 2008/0279738 | A1 | 11/2008 | Strehlau et al. | |
| 2008/0293989 | A1 | 11/2008 | Khanmamedova et al. | |
| 2012/0215043 | A1 * | 8/2012 | Gaffney | B01J 29/064 585/241 |

FOREIGN PATENT DOCUMENTS

| | | |
|---|---|---|
| WO | 2011053747 | 5/2011 |
| WO | 2012020743 | 2/2012 |

OTHER PUBLICATIONS

Sayed, M.B. et al.; Effect of impregnation of ZSM-5 with H3B03 on its acidity: A microcalorimetric study of NH3 adsorption; Applied Catalysis; vol. 23, No. 1; pp. 49-61; May 1, 1986.

(Continued)

*Primary Examiner* — Elizabeth Wood

(57) ABSTRACT

A catalyst for the dehydroaromatization of lower alkanes comprising boron in an amount of less than 1 wt % is supported on an inorganic support. The catalyst is useful in the production of aromatics from lower alkanes.

4 Claims, 4 Drawing Sheets

(56) References Cited

OTHER PUBLICATIONS

Zakumbaeva, G.D. et al.; "Conversion of an ethylene-pentane mixture over a molybdenum- and boron-promoted zeolite catalyst"; Petroleum Chemistry, Nauka/Interperiodica, Mo; vol. 52, No. 6; pp. 410-415; Nov. 6, 2012.

Simon, Mark et al.; "Isomerization reactions of n-0butenes over ismorphously substituted B/Al-ZSM-11 zeolites"; Microporous Materials; vol. 2, No. 5; pp. 477-486; Jun. 1, 1994.

Akhmetoc, A.F. et al.; "Modified pentasil-containing catalysts for aromatization of hydrocarbon gases" Chemistry and Technology of Fuels and Oils, Kluwer Academic Publishers-Lenum Publisher, NE; vol. 37, No. 5; pp. 347-353; Jan. 1, 2001.

\* cited by examiner

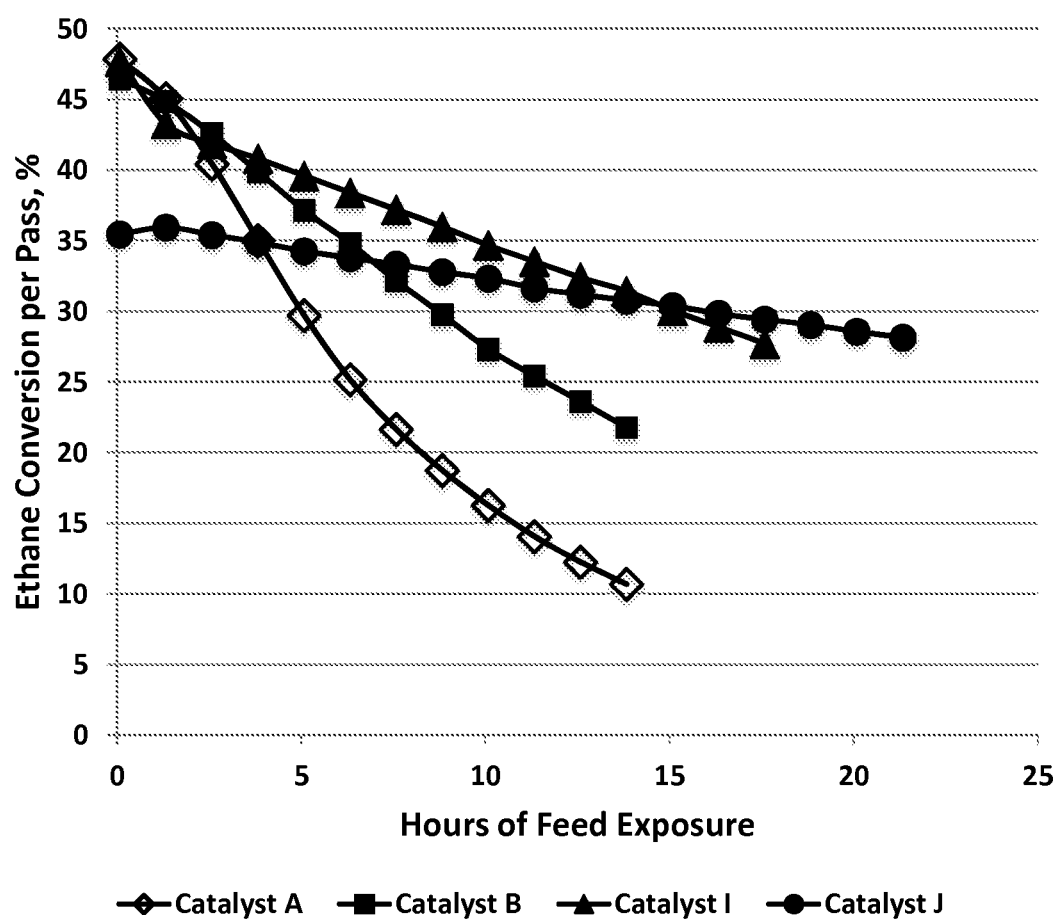

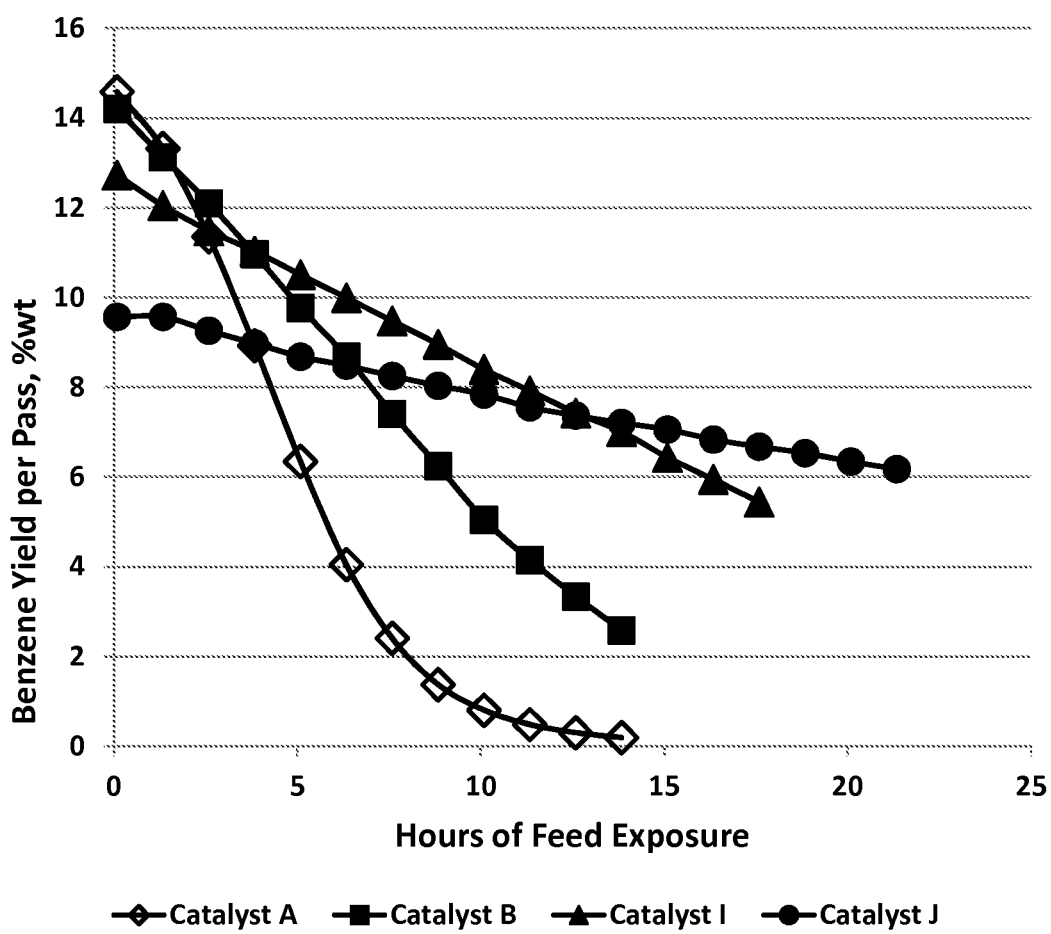

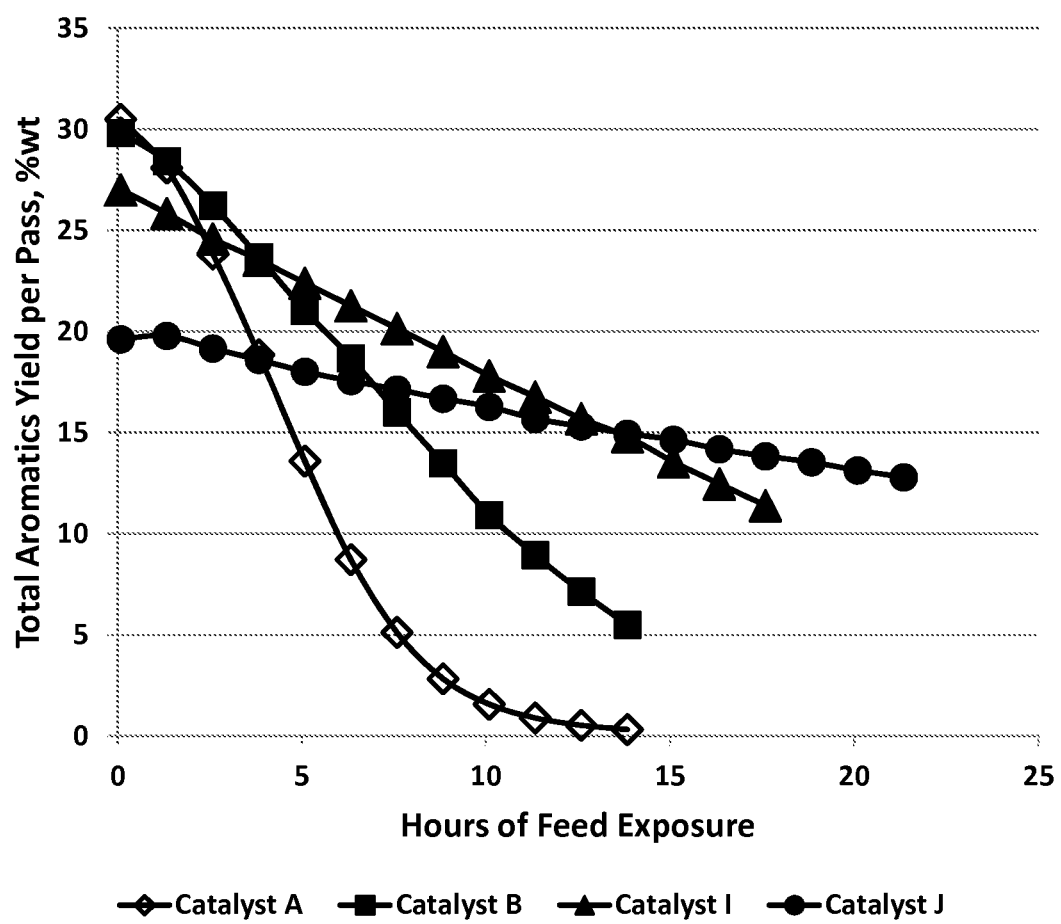

US 9,861,967 B2

DEHYDROAROMATIZATION CATALYST, METHOD OF MAKING AND USE THEREOF

PRIORITY CLAIM

The present application is the National Stage (§371) of International Application No. PCT/US2013/075550, filed Dec. 17, 2013, which claims priority from U.S. Provisional Application No. 61/739,089, filed Dec. 19, 2012 incorporated herein by reference.

FIELD OF THE INVENTION

The invention provides a catalyst that is useful for the dehydroaromatization of alkanes to form aromatic compounds. The catalyst comprises boron.

BACKGROUND OF THE INVENTION

There is a projected global shortage for benzene which is needed in the manufacture of key petrochemicals such as styrene, phenol, nylon and polyurethanes, among others. Generally, benzene and other aromatic hydrocarbons are obtained by separating a feedstock fraction which is rich in aromatic compounds, such as reformates produced through a catalytic reforming process and pyrolysis gasolines produced through a naphtha cracking process, from non-aromatic hydrocarbons using a solvent extraction process.

In an effort to meet growing world demand for benzene and other aromatics, various industrial and academic researchers have been working for several decades to develop catalysts and processes to make light aromatics (benzene, toluene, xylenes, or BTX) from cost-advantaged, light paraffin (C1-C4) feeds. Prior-art catalysts devised for this application usually contain an acidic zeolite material such as ZSM-5 and one or more metals such as Pt, Ga, Zn, Mo, etc. to provide a dehydrogenation function. Aromatization of ethane and other lower alkanes is thermodynamically favored at high temperature and low pressure without addition of hydrogen to the feed. Unfortunately, these process conditions are also favorable for rapid catalyst deactivation due to formation of undesirable surface coke deposits which block access to the active sites.

For many hydrocarbon processing applications, one approach to reducing catalyst performance decline rates due to coking is to increase the catalyst metals loading in an effort to promote faster hydrogenation/breakup of large coke precursor molecules on the surface. Another approach involves incorporation of additives such as phosphate or rare earths to moderate surface acidity and reduce coking rates under reaction conditions. These approaches are appropriate for processes featuring fixed or slowly-moving catalyst beds wherein the average catalyst particle residence time in the reactor zone between regenerations (coke burnoff steps) is relatively long (at least several days). For example, see U.S. Pat. Nos. 4,855,522 and 5,026,937, which describe ZSM-5-type lower-alkane aromatization catalysts promoted with Ga and additionally containing either a rare earth metal or a phosphorus-containing alumina, respectively.

Yet another approach to circumvent this problem is to devise a lower alkane aromatization process in which the catalyst spends a relatively short time (less than a day) under reaction conditions before being subjected to coke burnoff and/or other treatment(s) aimed at restoring all or some of the original catalytic activity. An example of such a process is one featuring two or more parallel reactors containing fixed or stationary catalyst beds, with at least one reactor offline for catalyst regeneration at any given time, while the other reactor(s) is/are processing the lower alkane feed under aromatization conditions to make aromatics. Another example of such a process features a fluidized catalyst bed, in which catalyst particles cycle rapidly and continuously between a reaction zone where aromatization takes place and a regeneration zone where the accumulated coke is burned off the catalyst to restore activity. For example, U.S. Pat. No. 5,053,570 describes a fluid-bed process for converting lower paraffin mixtures to aromatics.

Requirements for optimal catalyst performance in a process involving a relatively short period of catalyst exposure to reaction conditions between each regeneration treatment, such as a fluidized-bed process, can differ from those of fixed- or moving-bed processes which require longer catalyst exposure time to reaction conditions between regeneration treatments. Specifically, in processes involving short catalyst exposure times, it is important that the catalyst not exhibit excessive initial cracking or hydrogenolysis activity which could convert too much of the feedstock to undesirable, less-valuable byproducts such as methane.

It would be advantageous to develop a catalyst that exhibits a high aromatics yield and alkane conversion while also having a reduced performance decline over time.

SUMMARY OF THE INVENTION

The invention provides a catalyst for the dehydroaromatization of lower alkanes comprising boron wherein the boron is present in an amount of less than 1 wt % supported on an inorganic support.

The invention further provides a method of preparing a dehydroaromatization catalyst comprising: preparing an inorganic support, impregnating the support with boron or a compound thereof such that the amount of boron present on the support is in the range of from 0.005 wt % to 1 wt %; and drying and calcining the impregnated support.

The invention also provides a process for producing aromatic hydrocarbons which comprises: contacting one or more lower alkanes with a dehydroaromatization catalyst in a reactor, said catalyst comprising: about 0.005 to about 1% wt boron, about 10 to about 99.9% wt of an aluminosilicate, and a binder; and collecting the products from the contacting step and separating and recovering C6+ aromatic hydrocarbons.

BRIEF DESCRIPTION OF THE DRAWINGS

FIG. 2 depicts the ethane conversion obtained in Performance Tests 11-14.

FIG. 3 depicts the benzene yield obtained in Performance Tests 11-14.

FIG. 4 depicts the total aromatics yield obtained in Performance Tests 11-14.

DETAILED DESCRIPTION OF THE INVENTION

Figure 1:
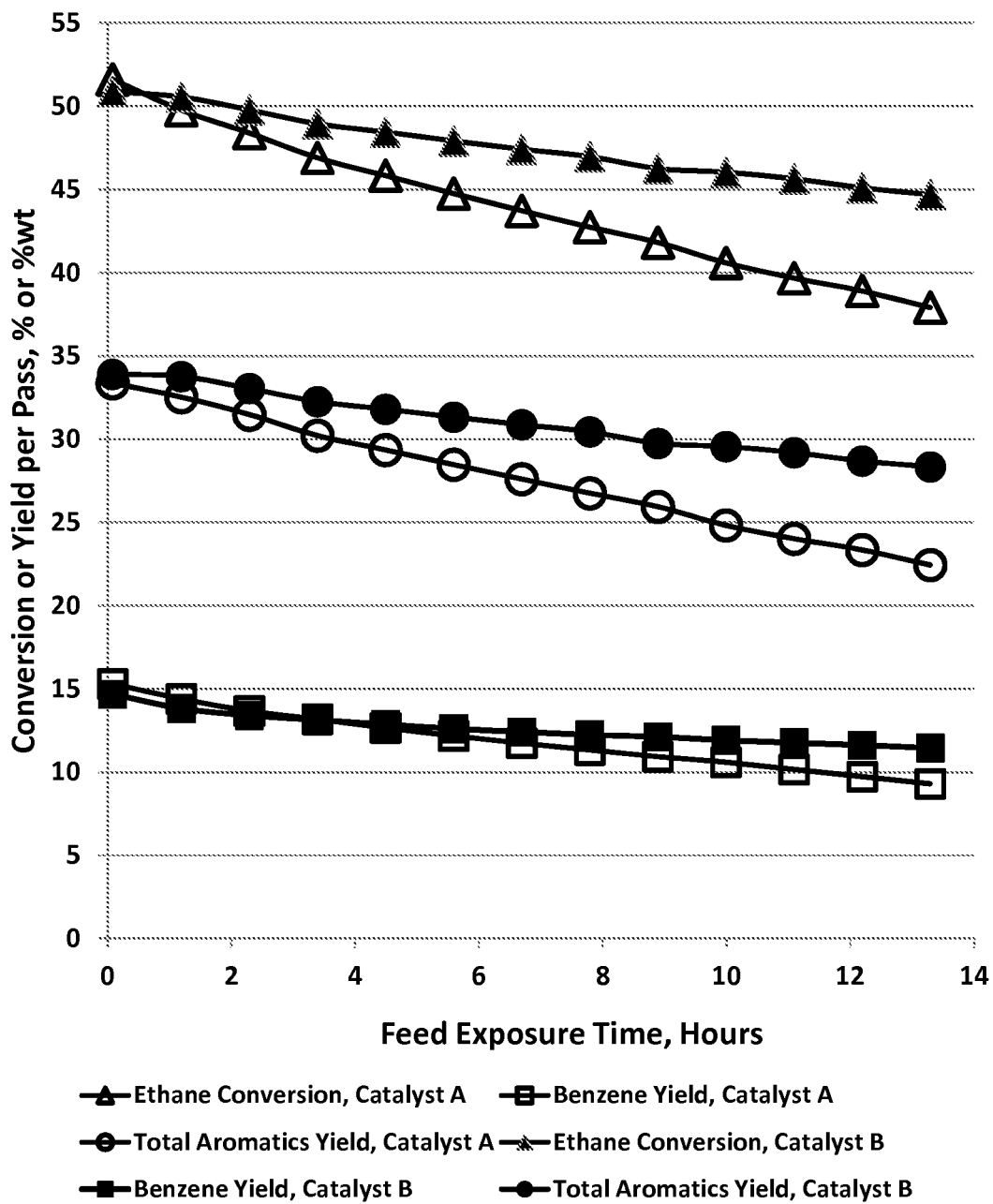
FIG. 1 depicts the ethane conversion, benzene yield, and total aromatics yield obtained in Performance Tests 1 and 2 in Example 1.

The present invention provides a catalyst useful in a process for producing aromatic hydrocarbons. The process comprises bringing a hydrocarbon feedstock containing at least about 50 percent by weight of ethane or other C2 hydrocarbons or other lower alkanes into contact with a dehydroaromatization catalyst comprising boron to promote the reaction of lower alkanes to aromatic hydrocarbons such as benzene at a temperature of about 550 to about 730° C. and a pressure of about 0.01 to about 1.0 MPa. The primary desired products of the process of this invention are benzene, toluene and xylene.

The hydrocarbons in the feedstock may be ethane, ethylene or other lower alkanes or mixtures thereof. Preferably, the majority of the feedstock is ethane and from about 0 to about 20 weight percent of the feedstock may be comprised of ethylene, preferably about 5 to about 10 weight percent. Lower alkanes may be ethane, propane, butane, pentane, etc. The feedstock may contain in addition up to about 40 weight percent of other open chain hydrocarbons containing between 3 and 8 carbon atoms as coreactants. Specific examples of such additional coreactants are propylene, isobutane, n-butenes and isobutene. The hydrocarbon feedstock preferably contains at least about 60 percent by weight of ethane or lower alkanes, more preferably at least about 70 percent by weight. The reaction feed is often referred to herein as ethane for convenience but it is meant to include all of the other hydrocarbon materials referred to above if it is necessary or desired for them to be present.

In a preferred embodiment, the reactor comprises a zone, vessel, or chamber containing catalyst particles through which the ethane-containing feed flows and the reaction takes place. The reactor system may involve a fixed, moving, or fluidized catalyst bed. The reaction products then flow out of the bed and are collected. The reaction products are then separated and C6+ aromatic hydrocarbons are recovered. Optionally, methane and hydrogen are recovered and optionally the C2-5 hydrocarbons are recycled to step (a).

A fixed bed reactor is a reactor in which the catalyst remains stationary in the reactor and the catalyst particles are arranged in a vessel, generally a vertical cylinder, with the reactants and products passing through the stationary bed. In a fixed bed reactor the catalyst particles are held in place and do not move with respect to a fixed reference frame. The fixed bed reactor may be an adiabatic single bed, a multi-tube surrounded with heat exchange fluid or an adiabatic multi-bed with internal heat exchange, among others. Fixed bed reactors are also referred to as packed bed reactors. Fixed bed reactors provide excellent gas solids contacting. The fixed bed reactor configuration may include at least two separate fixed beds in different zones so that at least one bed can be in active operation under reaction conditions while the catalyst in the other bed(s) is being regenerated.

In a moving bed catalytic reactor, gravity causes the catalyst particles to flow while maintaining their relative positions to one another. The bed moves with respect to the wall of the vessel in which it is contained. The reactants may move through this bed with cocurrent, countercurrent or crossflow. Plug flow is the preferred mode. The moving bed offers the ability to withdraw catalyst particles continuously or intermittently so they can be regenerated outside the reactor and reintroduced into the circuit later on. Thus, there is an advantage to using a moving bed when the catalyst has a short active life and can be continuously regenerated. A moving bed reactor may consist of at least one tray as well as supporting means for one or more catalyst beds. The supporting means may be permeable to gas and impermeable to catalyst particles.

A fluidized bed reactor is a type of reactor that may be used to carry out a variety of multiphase chemical reactions. In this type of a reactor, a gas is passed through the particulate catalyst at high enough velocities to suspend the solid and cause it to behave as though it were a fluid. The catalyst particles may be supported by a porous plate. The gas may be forced through the porous plate up through the solid material. At lower gas velocities the solids remain in place as the gas passes through the voids in the material. As the gas velocity is increased, the reactor reaches the stage where the force of the fluid on the solids is enough to balance the weight of the solid material and above this velocity the contents of the reactor bed begin to expand and swirl around much like an agitated tank or boiling pot of water. A fluidized bed reactor is preferred for use in the present invention because it provides uniform particle mixing, uniform temperature gradients and the ability to operate the reactor in a continuous state. The catalyst leaves the reaction zone with the reaction products and is separated therefrom in order to be regenerated before being recycled to the reaction zone.

The ethane contact time may range from about 0.1 second to about 1 minute. The ethane contact time is the average amount of time that one molecule of the ethane feed is in the reaction zone. The preferred ethane contact time is from about 1 to about 5 seconds. Longer ethane contact times are less desirable because they tend to allow for secondary reactions that lead to less-desirable byproducts such as methane and reduce selectivity to benzene and/or total aromatics.

The catalyst comprises from about 0.005 to about 0.09% wt platinum, basis the metal. The platinum is highly active in terms of catalyzing not only the desired dehydroaromatization reaction but also an undesired hydrogenolysis reaction leading to lower-value byproduct methane, so it is best if its concentration in the catalyst not be more than 0.1% wt because otherwise too much methane will be produced. In one embodiment from about 0.005 to about 0.05% wt of platinum is used.

An attenuating metal or metals may also be added to the catalyst of the present invention. While the attenuating metal may have catalytic activity in its own right, its main function is to moderate the catalytic activity of platinum so as to reduce the production of less-valuable methane byproduct. Examples of suitable attenuating metals include but are not limited to tin, lead, germanium, and gallium. The attenuating metal comprises not more than about 0.5% wt of the catalyst, basis the metal, more preferably not more than about 0.2% wt and most preferably not more than about 0.1% wt of the attenuating metal is utilized because more than that can cause the overall conversion to aromatics to become too low for commercial use.

The catalyst comprises boron in an amount of less than 1 wt %. The amount of boron may be in the range of from 0.005 to 1 wt %, preferably from 0.01 to 0.6 wt %, more preferably from 0.02 to 0.4 wt %.

The catalyst also comprises from about 10 to about 99.9% wt of one or more aluminosilicate materials, preferably from about 30 to about 99.9% wt, basis the aluminosilicate(s). The aluminosilicates preferably have a silicon dioxide: aluminum trioxide ($SiO_2:Al_2O_3$) molar ratio of from about 20 to about 80. The aluminosilicates may preferably be zeolites having the MFI or MEL type structure and may be ZSM-5, ZSM-8, ZSM-11, ZSM-12 or ZSM-35. The zeolite or zeolite mixture is preferably converted to H+ form to provide sufficient acidity to help catalyze the dehydroaromatization reaction. This can be accomplished by calcining the ammonium form of the zeolite in air at a temperature of at least about 400° C.

The binder material serves the purpose of holding individual zeolite crystal particles together to maintain an overall catalyst particle size in the optimal range for fluidized-bed operation or to prevent excessive pressure drop in fixed or moving bed operation. The binder may be selected from the group consisting of alumina, silica, silica/alumina, various clay materials such as kaolin, or mixtures thereof. Preferably, amorphous inorganic oxides of gamma alumina, silica, silica/alumina or a mixture thereof may be included. Most preferably, alumina and/or silica are used as the binder material.

A boron containing crystalline aluminosilicate, such as ZSM-5, may be synthesized by preparing the aluminosilicate containing the aluminum and silicon in the framework, depositing boron on the aluminosilicate and then calcining the aluminosilicate. The platinum and/or attenuating metal may also be added by the same procedure, either prior to, simultaneously with, or after the addition of boron. The metals may be added by any commonly known method for adding metals to such structures including incorporation into the aluminosilicate framework during crystal synthesis, or subsequent ion exchange into an already-synthesized crystal framework, or well as by various impregnation methods known to those skilled in the art. The boron, platinum and attenuating metal may be added by the same or different methods.

In a preferred embodiment, the crystalline aluminosilicate is calcined to remove moisture. Then, the aluminosilicate is impregnated with boron by contacting the aluminosilicate with an aqueous solution comprising boron. This aqueous solution is preferably an aqueous solution of boric acid. The aluminosilicate is calcined again, and then the platinum and attenuating metal are added by impregnation with an aqueous solution comprising platinum and the attenuating metal. When the attenuating metal is gallium, this aqueous solution is preferably an aqueous solution of tetraammine platinum nitrate and gallium (III) nitrate.

In a preferred embodiment of the present invention an ethane or lower alkane feedstream is introduced into the dehydroaromatization reactor. The feedstream then comes into contact with the catalyst particles for the prescribed period of time. The reaction products leave the reactor and are transferred into a separator. The separator removes the aromatic products and the principal byproducts, methane and hydrogen, which preferably may be recovered, and also removes C2-5 byproducts and unreacted ethane or other lower alkanes which optionally may be recycled to the dehydroaromatization reactor.

The following examples are provided for illustrative purposes only and are not intended to limit the scope of the invention.

Example 1

Catalyst A was made on 1.6 mm diameter cylindrical extrudate particles containing 80% wt of zeolite ZSM-5 CBV 2314 powder (23:1 molar SiO2/Al2O3 ratio, available from Zeolyst International) and 20% wt alumina binder. The extrudate samples were calcined in air up to 650° C. to remove residual moisture prior to use in catalyst preparation, according to the following temperature program: hold 10 min at 100° C., increase temperature from 100 to 650° C. at 3° C./min, hold 3 hrs at 650° C., then cool to 100° C.

For catalyst preparation, metals were deposited on 25-100 gram samples of the above ZSM-5/alumina extrudate by first combining appropriate amounts of stock aqueous solutions of tetraammine platinum nitrate and gallium(III) nitrate, diluting this mixture with deionized water to a volume just sufficient to fill the pores of the extrudate, and impregnating the extrudate with this solution at room temperature and atmospheric pressure. Impregnated samples were aged at room temperature for 2-3 hours and then dried overnight at 100° C. The target metal loadings for Catalyst A were 0.09% w Pt and 0.25% wt Ga. No boron compound was used in the preparation of Catalyst A; hence, catalyst A was not made according to the present invention.

Catalyst B, prepared according to the present invention, was made with the same materials and procedures as Catalyst A, except that the 650° C.-calcined extrudate was subjected to an initial pore volume impregnation with an aqueous boric acid solution, aged at room temperature for 2-3 hrs, dried overnight at 100° C., then calcined in air up to 650° C. After this second calcination step, the extrudate containing boron was impregnated with an aqueous solution of tetraammine platinum nitrate and gallium nitrate in the manner described above for Catalyst A. The impregnated sample was aged at room temperature for 2-3 hours, then dried overnight at 100° C. The target metal loadings for Catalyst B were 0.09% wt Pt, 0.25% wt Ga, and 0.10% wt B.

Samples of Catalysts A and B, prepared as described above, were tested in Performance Tests 1 and 2, respectively. For each performance test, a 15-cc charge of fresh (not previously tested) catalyst was loaded into a quartz tube (1.40 cm inner diameter) and positioned in a three-zone furnace connected to an automated gas flow system.

Prior to Performance Tests 1 and 2, the catalyst charges were pretreated in situ at atmospheric pressure (approximately 0.1 MPa absolute) in the following manner:

(a) calcination with air at approximately 60 liters per hour (L/hr), during which the reactor wall temperature was raised from 25 to 510° C. in 12 hrs, held at 510° C. for 4 hrs, then further increased from 510° C. to 621° C. in 1 hr, then held at 621° C. for 30 min;

(b) nitrogen purge at approximately 60 L/hr, 621° C., for 20 min;

(c) reduction with hydrogen at 60 L/hr, 621° C., for 30 min.

At the end of the above pretreatment, the catalyst charges were subjected to 157 cycles of alternating exposure to 100% ethane feed and 100% hydrogen at atmospheric pressure (ca. 0.1 MPa) and 621° C. reactor wall temperature according to the following protocol:

(a) 5 minutes of 100% ethane feed at 1000 GHSV (b) 10 minutes of 100% hydrogen at 4000 GHSV.

The total cumulative exposure time of the catalyst to ethane feed under this test regime was 13.3 hrs. The total runtime for the 157 ethane feed/hydrogen stripping cycles described above was 39.9 hrs.

To monitor changes in catalyst performance during these tests, the total outlet stream of each reactor was sampled and analyzed approximately once every 3 hrs, near the end of selected 5-minute ethane exposure intervals, by an online gas chromatographic analyzer system. Based on the composition data obtained from the gas chromatographic analysis, ethane conversion was calculated according to the following formula:

$$\% \text{ ethane conversion} = 100 - \% \text{ wt ethane in outlet stream.}$$

Yields per pass of each individual product component were given by the % wt amount of the product in the reactor outlet stream. Normalized yields of each product component were calculated according to the following formula:

$$\text{Normalized yield of product } P = (100 * \% \text{ wt yield per pass of product } P)/\% \text{ ethane conversion.}$$

At the end of the tests, the ethane flow to the reactor was terminated, and hydrogen was re-introduced at a flow rate of 60 L/hr. The reactor furnace heaters were turned off, and the catalyst was allowed to cool to about 38° C. over a period of approximately 8 hrs.

The ethane conversion, benzene yield, and total aromatics yield data obtained in Performance Tests 1 and 2 are compared in FIG. 1. As shown in this figure, Catalyst B, prepared according to the present invention, exhibited significantly lower performance decline rates than Catalyst A with respect to ethane conversion level, benzene yield, and total aromatics yield. Specifically, initial and final ethane conversion levels measured for Catalyst B under these test conditions were 50.9 and 44.7%, respectively, while the corresponding values for Catalyst A were 51.6 and 37.9%, respectively. Initial and final benzene yields obtained with Catalyst B were 14.7 and 11.5% wt, respectively, compared with 15.3 and 9.3% wt, respectively, for Catalyst A. Initial and final total aromatics yields obtained with Catalyst B were 33.9 and 28.3% wt, respectively, compared with 33.4 and 22.4% wt, respectively, for Catalyst A.

In addition, the average ethane conversion levels and normalized product yields obtained over the entire run period for Performance Test 1 and Performance Test 2 are listed in Table 1 below.

TABLE 1

| | PERFORMANCE TEST | |
|---|---|---|
| | 1 | 2 |
| | CATALYST | |
| | A | B |
| Average ethane conversion, % | 44.04 | 47.58 |
| Average Normalized Yields, % wt | | |
| Hydrogen | 9.66 | 9.92 |
| Methane | 13.50 | 12.36 |
| Ethylene | 9.80 | 8.74 |
| Propylene | 1.67 | 1.53 |
| Propane | 2.17 | 1.95 |
| C4 Compounds | 0.40 | 0.37 |
| C5 Compounds | 0.05 | 0.04 |
| Benzene | 26.96 | 26.49 |
| Toluene | 18.81 | 21.86 |
| C8 Aromatics | 4.35 | 4.99 |
| C9+ Aromatics | 12.64 | 11.74 |
| Total Aromatics | 62.75 | 65.08 |

As shown in Table 1, Catalyst B, made according to the present invention, showed not only a higher average ethane conversion rate (consistent with its lower performance decline rate shown in FIG. 1) but also gave a higher normalized yield of total aromatics relative to Catalyst A under the test conditions used here.

Example 2

Catalyst C was prepared with the same materials and procedures as those used to make Catalyst A in Example 1, except that the aqueous impregnating solution contained boric acid in addition to tetraammine platinum nitrate and gallium nitrate. The impregnated extrudate was aged at room temperature for 2-3 hours, then dried overnight at 100° C. Target metal loadings for Catalyst C were 0.09% wt Pt, 0.25% wt Ga, and 0.05% wt B.

Catalyst D was prepared with the same materials, procedures, and target metal loadings as those of Catalyst C, except that, after the post-impregnation drying step at 100° C., Catalyst D was calcined in air up to 650° C. according to the following temperature program: hold 10 min at 100° C., increase temperature from 100 to 650° C. at 3° C./min, hold 3 hrs at 650° C., then cool to 100° C.

15-cc fresh charges of Catalysts C and D were subjected to Performance Tests 3 and 4, respectively. Performance Tests 3 and 4 were conducted using the same feed, operating conditions, and procedures as those used for Performance Tests 1 and 2 in Example 1 above. Average ethane conversion levels and normalized product yields obtained over the entire run period for Performance Tests 3 and 4 are listed in Table 2 below. The corresponding data from Performance Test 1 are also shown in Table 2 for comparison.

TABLE 2

| | PERFORMANCE TEST | | |
|---|---|---|---|
| | 1 | 3 | 4 |
| | CATALYST | | |
| | A | C | D |
| Average ethane conversion, % | 44.04 | 45.62 | 47.39 |
| Average Normalized Yields, % wt | | | |
| Hydrogen | 9.66 | 9.77 | 10.02 |
| Methane | 13.50 | 12.54 | 11.48 |
| Ethylene | 9.80 | 10.37 | 9.24 |
| Propylene | 1.67 | 1.71 | 1.63 |
| Propane | 2.17 | 2.00 | 1.97 |
| C4 Compounds | 0.40 | 0.43 | 0.41 |
| C5 Compounds | 0.05 | 0.07 | 0.06 |
| Benzene | 26.96 | 26.88 | 26.54 |
| Toluene | 18.81 | 20.14 | 22.26 |
| C8 Aromatics | 4.35 | 4.76 | 5.27 |
| C9+ Aromatics | 12.64 | 11.32 | 11.13 |
| Total Aromatics | 62.75 | 63.11 | 65.19 |

As shown in Table 2, Catalyst D, made according to the present invention with addition of a boron compound followed by a high-temperature calcination, gave a higher average ethane conversion rate and higher normalized total aromatics yield than Catalysts A or C under the test conditions employed here.

Example 3

Catalyst E was made with the same materials and procedures as those used to make Catalyst A in Example 1 above, except that the target metal loadings for Catalyst E were 0.025% w Pt and 0.09% wt Ga. No boron compound was used in the preparation of Catalyst E; hence, catalyst E was not made according to the present invention.

Catalyst F was made with the same materials and procedures as those used to make Catalyst B in Example 1 above, except that target metal loadings for Catalyst F were 0.025% wt Pt, 0.09% wt Ga, and 0.10% wt B.

Catalyst G was made with the same materials and procedures as those used to make Catalyst C in Example 2 above, except that target metal loadings for Catalyst G were 0.025% wt Pt, 0.09% wt Ga, and 0.05% wt B.

Catalyst H was made with the same materials and procedures as those used to make Catalyst D in Example 2 above, except that target metal loadings for Catalyst H were 0.025% wt Pt, 0.09% wt Ga, and 0.05% wt B.

15-cc fresh charges of Catalysts E, F, G, and H were subjected to Performance Tests 5, 6, 7, and 8, respectively. Performance Tests 5-8 were conducted using the same feed, operating conditions, and procedures as those used for Performance Tests 1-4 in Examples 1 and 2 above. Average ethane conversion levels and normalized product yields obtained over the entire run period for Performance Tests 5-8 are listed in Table 3 below.

TABLE 3

|  | PERFORMANCE TEST | | | |
|---|---|---|---|---|
|  | 5 | 6 | 7 | 8 |
|  | CATALYST | | | |
|  | E | F | G | H |
| Average ethane conversion, % | 44.08 | 43.96 | 42.51 | 42.42 |
| Average Normalized Yields, % wt | | | | |
| Hydrogen | 9.63 | 9.70 | 9.55 | 9.89 |
| Methane | 12.26 | 12.07 | 13.02 | 10.83 |
| Ethylene | 11.89 | 11.05 | 11.07 | 11.11 |
| Propylene | 2.19 | 2.11 | 2.01 | 2.10 |
| Propane | 2.26 | 2.31 | 2.38 | 2.50 |
| C4 Compounds | 0.52 | 0.50 | 0.48 | 0.51 |
| C5 Compounds | 0.07 | 0.07 | 0.07 | 0.08 |
| Benzene | 27.08 | 26.97 | 27.45 | 27.39 |
| Toluene | 19.42 | 20.66 | 19.15 | 21.04 |
| C8 Aromatics | 4.69 | 4.93 | 4.69 | 5.41 |
| C9+ Aromatics | 9.98 | 9.62 | 10.13 | 9.15 |
| Total Aromatics | 61.18 | 62.18 | 61.43 | 62.99 |

As shown in Table 3, Catalysts F and H, made according to the present invention, gave higher normalized total aromatics yields under these test conditions than Catalysts E and G.

Example 4

Catalyst I was made with the same materials and procedures as those used to make Catalyst B in Example 1 above, except that target metal loadings for Catalyst I were 0.09% wt Pt, 0.25% wt Ga, and 0.20% wt B.

15-cc fresh charges of Catalyst A (prepared as described in Example 1 above) and Catalyst I were subjected to Performance Tests 9 and 10, respectively. Performance Tests 9 and 10 were conducted in the same manner as Performance Tests 1-8 described in Examples 1-3 above, with the following exceptions:
a) The final pretreatment temperature was 580° C. instead of 621° C.
b) The hydrocarbon feed consisted of 50% wt each of ethane and propane instead of 100% ethane; total hydrocarbon feed rate was 1000 GHSV.
c) The reactor wall temperature was held at 580° C. instead of 621° C. during the run.
d) The number of 5/10 minute feed/$H_2$ cycles was 313 instead of 157. Thus, the total hydrocarbon feed exposure time was 26.08 hrs instead of 13.3 hrs.

To monitor changes in catalyst performance during these tests, the total outlet stream of each reactor was sampled and analyzed approximately once every 3 hrs, near the end of selected 5-minute ethane exposure intervals, by an online gas chromatographic analyzer system. Based on the composition data obtained from the gas chromatographic analysis, net ethane and propane conversion levels were calculated according to the following formulas:

% ethane conversion=100×(% wt ethane in feed−% wt ethane in outlet stream)/(% wt ethane in feed).

% propane conversion=100×(% wt propane in feed−% wt propane in outlet stream)/(% wt propane in feed).

% total ethane+propane conversion=((% wt ethane in feed×% ethane conversion)+(% wt propane in feed×% propane conversion))/100

Yields per pass of each individual product component were given by the % wt amount of the product in the reactor outlet stream. Normalized yields of each product component were calculated according to the following formula:

Normalized yield of product P=(100*% wt yield per pass of product P)/(% total ethane+propane conversion).

Average feed conversion levels and normalized product yields obtained over the entire run period for Performance Tests 9 and 10 are listed in Table 4 below.

TABLE 4

|  | PERFORMANCE TEST | |
|---|---|---|
|  | 9 | 10 |
|  | CATALYST | |
|  | A | I |
| Average ethane conversion, % | −6.34 | −7.96 |
| Average propane conversion, % | 95.14 | 94.43 |
| Average total ethane + propane conversion, % | 44.38 | 43.22 |
| Average Normalized Yields, % wt | | |
| Hydrogen | 6.94 | 7.92 |
| Methane | 18.65 | 12.73 |
| Ethylene | 4.72 | 4.69 |
| Propylene | 2.20 | 2.47 |
| C4 Compounds | 0.39 | 0.40 |
| C5 Compounds | 0.05 | 0.05 |
| Benzene | 28.73 | 30.27 |
| Toluene | 24.88 | 26.68 |
| C8 Aromatics | 7.61 | 9.80 |
| C9+ Aromatics | 5.83 | 4.98 |
| Total Aromatics | 67.06 | 71.74 |

As shown in Table 4, the normalized total aromatics yields for Catalyst I, made according to the present invention, was over four percentage points greater than that of Catalyst A under the test conditions used here.

Example 5

Catalyst J was made with the same materials and procedures as those used to make Catalyst B in Example 1 above, except that target metal loadings for Catalyst I were 0.09% wt Pt, 0.25% wt Ga, and 0.30% wt B.

15-cc fresh charges of Catalyst A (prepared as described in Example 1 above), Catalyst B (prepared as described in Example 1 above), Catalyst I (prepared as described in Example 4 above), and Catalyst J were subjected to Performance Tests 11-14, respectively. Performance Tests 11-14 were conducted with the same pretreatment procedure as was used in Performance Tests 1 and 2 described in Example 1 above.

At the end of the pretreatment period, the catalysts were subjected to continuous exposure to 100% ethane feed at 1000 GHSV, 0 barg pressure, 621° C. reactor wall temperature. Test run lengths ranged from about 13.8 to about 21.3 hours of feed exposure. For each test, online gas chromatographic sampling of the total reactor outlet stream began at 5 minutes onstream and continued approximately once every 1.25 hrs thereafter until the run was terminated. Based on the composition data obtained from the gas chromatographic analysis, ethane conversion levels, per-pass product yields, and normalized product yields were calculated as described in Example 1 above.

The ethane conversion, per-pass benzene yield, and per-pass total aromatics yield data obtained in Performance Tests 11-14 are compared in FIGS. 2-4, respectively.

As shown in FIGS. 2-4, Catalysts B, I, and J, prepared according to the present invention, exhibited significantly lower performance decline rates than Catalyst A with respect to ethane conversion level, benzene yield, and total aromatics yield. The initial and final values obtained for ethane conversion, benzene yield, and total aromatics yield in these tests are summarized in Table 5 below.

TABLE 5

| | PERFORMANCE TEST | | | |
|---|---|---|---|---|
| | 11 | 12 | 13 | 14 |
| | CATALYST | | | |
| | A | B | I | J |
| Hours Tested | 13.83 | 13.83 | 17.58 | 21.33 |
| Initial Ethane Conversion, % | 47.85 | 46.47 | 47.70 | 35.45 |
| Final Ethane Conversion, % | 10.67 | 21.77 | 27.72 | 28.13 |
| Initial Benzene Yield per Pass, % wt | 14.59 | 14.21 | 12.73 | 9.57 |
| Final Benzene Yield per Pass, % wt | 0.19 | 2.58 | 5.44 | 6.18 |
| Initial Total Aromatics Yield per Pass, % wt | 30.49 | 29.82 | 27.00 | 19.62 |
| Final Total Aromatics Yield per Pass, % wt | 0.33 | 5.51 | 11.40 | 12.80 |

Average ethane conversion levels and normalized product yields obtained during Performance Tests 11-14 are listed in Table 6 below.

TABLE 6

| | PERFORMANCE TEST | | | |
|---|---|---|---|---|
| | 11 | 12 | 13 | 14 |
| | CATALYST | | | |
| | A | B | I | J |
| Test run length, hrs | 13.83 | 13.83 | 17.58 | 21.33 |
| Average ethane conversion, % | 26.40 | 33.82 | 38.07 | 32.05 |
| Average Normalized Yields, % wt | | | | |
| Hydrogen | 8.15 | 9.03 | 9.23 | 9.08 |
| Methane | 6.62 | 8.95 | 10.01 | 8.56 |
| Ethylene | 46.10 | 25.14 | 19.39 | 23.23 |
| Propylene | 3.84 | 4.03 | 3.59 | 4.40 |
| Propane | 1.68 | 2.73 | 2.62 | 3.02 |
| C4 Compounds | 1.58 | 1.21 | 0.99 | 1.35 |
| C5 Compounds | 0.19 | 0.17 | 0.12 | 0.16 |
| Benzene | 15.18 | 22.65 | 25.42 | 24.23 |
| Toluene | 9.82 | 16.75 | 20.68 | 19.38 |
| C8 Aromatics | 2.21 | 3.72 | 4.09 | 4.12 |
| C9+ Aromatics | 4.62 | 5.61 | 3.87 | 2.46 |
| Total Aromatics | 31.84 | 48.73 | 54.05 | 50.20 |

As shown in Table 6, Catalysts B, I, and J, prepared according to the present invention, maintained significantly higher average ethane conversion and normalized benzene and total aromatics yields during these performance tests than Catalyst A, which was not prepared according to the present invention.

That which is claimed is:

1. A catalyst for the dehydroaromatization of lower alkanes comprising boron wherein the boron is present in an amount of less than 1 wt % supported on an inorganic support, wherein the catalyst is prepared by a method comprising:

preparing an aluminosilicate inorganic support, wherein the inorganic support does not comprise boron, impregnating the support with boron or a compound thereof such that the amount of boron present on the support is in the range of from 0.005 wt % to 1 wt %; and drying and calcining the impregnated support, wherein the catalyst comprises boron in an amount in the range of from 0.005 wt % to 1 wt %, wherein the catalyst further comprises platinum at a concentration of from 0.005 wt % to 1 wt %, wherein the catalyst further comprises gallium at a concentration of from 0.005 wt % to 1 wt %, and wherein the inorganic support contains at least 10 wt % of a zeolite selected from ZSM-5, ZSM-11, ZSM-12, ZSM-23, and ZSM-35.

2. The catalyst of claim 1 wherein the inorganic support contains ZSM-5.

3. The catalyst of claim 1 wherein the amount of boron is in the range of from 0.005 wt % to 0.5 wt %.

4. The catalyst of claim 1 wherein the amount of boron is in the range of from 0.05 wt % to 0.3 wt %.

* * * * *